US011992651B2

(12) United States Patent
Slaby et al.

(10) Patent No.: US 11,992,651 B2
(45) Date of Patent: May 28, 2024

(54) SYSTEMS AND METHODS FOR HEAD HEIGHT PRESSURE COMPENSATION

(71) Applicants: Baxter International Inc., Deerfield, IL (US); Baxter Healthcare SA, Glattpark (CH)

(72) Inventors: Jiri Slaby, Buffalo Grove, IL (US); Peter Bojan, Grayslake, IL (US); Slawomir Edward Wojtysiak, McHenry, IL (US)

(73) Assignees: BAXTER INTERNATIONAL INC., Deerfield, IL (US); BAXTER HEALTHCARE SA, Glattpark (CH)

( * ) Notice: Subject to any disclaimer, the term of this patent is extended or adjusted under 35 U.S.C. 154(b) by 0 days.

(21) Appl. No.: 17/877,305

(22) Filed: Jul. 29, 2022

(65) Prior Publication Data

US 2023/0038869 A1 Feb. 9, 2023

Related U.S. Application Data

(60) Provisional application No. 63/229,121, filed on Aug. 4, 2021.

(51) Int. Cl.
*A61M 5/168* (2006.01)
*A61M 5/142* (2006.01)
*A61M 5/172* (2006.01)

(52) U.S. Cl.
CPC .......... *A61M 5/1428* (2013.01); *A61M 5/142* (2013.01); *A61M 5/16877* (2013.01); *A61M 5/16881* (2013.01); *A61M 5/172* (2013.01); *A61M 2005/14264* (2013.01)

(58) Field of Classification Search
CPC .............. A61M 5/1414; A61M 5/1415; A61M 5/16877; A61M 5/172; A61M 5/142; A61M 2209/084; A61M 2209/086; A61M 2209/08; A61M 2205/3331; A61M 2205/3334; A61M 2005/14208; G16H 20/17

See application file for complete search history.

(56) References Cited

U.S. PATENT DOCUMENTS 7,575,564 B2 12/2009 Childers
9,474,842 B2 10/2016 Childers et al.
9,585,993 B2 3/2017 Childers et al.
(Continued)

OTHER PUBLICATIONS

International Preliminary Report on Patentability, PCT/US2022/038855 dated Jul. 10, 2023—15 pages.

*Primary Examiner* — Brandy S Lee
*Assistant Examiner* — Hong-Van N Trinh
(74) *Attorney, Agent, or Firm* — K&L Gates LLP

(57) ABSTRACT

The present disclosure provides a new and innovative method and system for flow rate compensation in devices, such as infusion pumps. In various embodiments, a computer-implemented method includes determining a location of a plurality of infusion pumps in a pump stack including the plurality of infusion pumps and a fluid supply connected to each of the plurality of infusion pumps. The computer-implemented method also includes determining a reference infusion pump, in the plurality of infusion pumps, and adjusting the flow rate for each infusion pump in the plurality of infusion pumps based on the distance between the infusion pump and the reference infusion pump.

10 Claims, 5 Drawing Sheets

(56) References Cited

U.S. PATENT DOCUMENTS

| | | |
|---|---|---|
| 2013/0083191 A1 | 4/2013 | Lowery et al. |
| 2016/0256628 A1* | 9/2016 | Lee .................... G05D 7/0617 |
| 2018/0147347 A1* | 5/2018 | Drost ................... A61M 5/172 |
| 2018/0228967 A1* | 8/2018 | Hopkins ........... A61M 5/16813 |
| 2022/0126020 A1* | 4/2022 | Abal ................ A61M 5/16831 |

* cited by examiner

| Pump # | h [inch] | Force [g] | Force difference [g] |
|---|---|---|---|
| 1 | 28.3 | 3.9 | N/A |
| 2 | 32.7 | 4.5 | 0.5900 |
| 3 | 37.0 | 5.0 | 1.1800 |
| 4 | 41.3 | 5.6 | 1.7700 |
| 5 | 45.7 | 6.2 | 2.3600 |
| 6 | 50.0 | 6.8 | 2.9500 |
| 7 | 54.3 | 7.4 | 3.5400 |
| 8 | 58.7 | 8.0 | 4.1300 |
| 9 | 63.0 | 8.6 | 4.7200 |
| 10 | 67.3 | 9.2 | 5.3100 |
| 11 | 71.7 | 9.8 | 5.9000 |
| 12 | 76.0 | 10.4 | 6.4900 |

FIG. 5

SYSTEMS AND METHODS FOR HEAD HEIGHT PRESSURE COMPENSATION

PRIORITY CLAIM

This application claims priority to and the benefit as a non-provisional application of U.S. Provisional Patent Application No. 63/229,121, filed Aug. 4, 2021, the entire contents of which are hereby incorporated by reference and relied upon.

TECHNICAL FIELD

The instant application is directed towards infusion pumps and more specifically to systems and methods for providing flow rate compensation to one or more infusion pumps with respect to a head height pressure of a fluid supply container.

BACKGROUND

The present disclosure provides a new and innovative method and system for flow control in electronic devices, including medical devices. In various embodiments, the device includes an infusion pump. Generally, patients sometimes require precise delivery of either continuous medication or medication at set periodic intervals. Medical pumps provide controlled drug infusion such that a drug can be administered at a precise rate to maintain a drug concentration within a therapeutic margin and out of an unnecessary or possibly toxic range. The medical pumps can provide appropriate drug delivery to a patient at a controllable rate, which does not require frequent attention.

Medical pumps may facilitate administration of intravenous therapy to patients both in and outside of a clinical setting. Outside a clinical setting, doctors have found that in many instances patients can return to substantially normal lives, provided they receive periodic or continuous intravenous administration of medication. Among the types of therapies requiring this kind of administration are antibiotic therapy, chemotherapy, pain control therapy, nutritional therapy, and several other types known by those skilled in the art. In many cases, patients receive multiple daily therapies. Certain medical conditions require infusion of drugs in solution over relatively short periods such as from thirty minutes to two hours. These conditions and others have combined to promote the development of increasingly lightweight, portable, or ambulatory infusion pumps that can be worn by a patient and are capable of administering a continuous supply of medication at a desired rate, or providing several doses of medication at scheduled intervals.

Configurations of infusion pumps include elastomeric pumps, which squeeze solution from flexible containers, such as balloons, into intravenous ("IV") tubing for delivery to a patient. Alternatively, spring-loaded pumps pressurize solution containers or reservoirs. Certain pump designs utilize cartridges containing flexible compartments that are squeezed by pressure rollers for discharging solutions. Infusion pumps utilizing syringes are also known. These pumps use a drive mechanism to move a plunger of a syringe to deliver fluid to a patient. Typically, these infusion pumps include a housing adapted to receive a syringe assembly, a drive mechanism adapted to move the syringe plunger, a pump control unit having a variety of operating controls, and a power source for powering the pump including the drive mechanism and controls.

Additionally, some infusion pumps are portable. For example, an infusion pump may be smaller and more compact for mobile use by ambulatory patients or other patients. Naturally, a portable pump must be supplied with an equally portable power source to power a pump motor. Batteries are a suitable choice of power for portable units. Some pumps may use disposable batteries while other pumps may use rechargeable batteries. The pump may also be sized for attachment to an IV pole. The IV pole, with attached pump, may remain stationary or may be moved about in a hospital setting. In another example, the pump may be attached to a hospital bed or other support structure. As noted above, the pump may be portable and may be carried by the patient, for example, in a pouch. Alternatively, the pump may be attached to and supported by the patient's clothing and/or other support apparel such as a belt, a vest, or the like.

Several methods exist to ensure that a medical device delivers medication at a specified rate. However, the existing methods have several disadvantages, limitations, and drawbacks. For example, existing methods require the devices to be within a particular distance of a fluid supply container such as an IV bag. This can be particularly problematic in situations where multiple devices are located in a stack and/or the devices are mobile relative to a fluid supply container. In these instances, when the distance between the fluid supply container and the medical device exceeds a threshold distance, the medical device may stop functioning and/or fail to deliver medication at a specified rate. Accordingly, a need exists for a system that adjusts a flow rate of medical devices based on a distance between a fluid supply container and the medical devices.

SUMMARY

The present disclosure provides a new and innovative method and system for flow rate compensation in medical devices, such as infusion pumps. In light of the disclosure set forth herein, and without limiting the disclosure in any way, in a first aspect of the present disclosure, which may be combined with any other aspect, or portion thereof, described herein a computer-implemented method includes determining a location of a plurality of infusion pumps in a pump stack including the plurality of infusion pumps and a fluid supply connected to each of the plurality of infusion pumps, determining a reference infusion pump, in the plurality of infusion pumps, and adjusting a flow rate for each infusion pump in the plurality of infusion pumps based on s distance between the infusion pump and the reference infusion pump.

In a second aspect of the present disclosure, which may be combined with any other aspect, or portion thereof, described herein, the fluid supply container comprises an IV bag.

In a third aspect of the present disclosure, which may be combined with any other aspect, or portion thereof, described herein, the distance between an infusion pump and the reference infusion pump is based on a tone generated by the reference infusion pump.

In a fourth aspect of the present disclosure, which may be combined with any other aspect, or portion thereof, described herein, the distance between an infusion pump and the reference infusion pump is determined based on the number of infusion pumps between the infusion pump and the reference infusion pump.

In a fifth aspect of the present disclosure, which may be combined with any other aspect, or portion thereof, described herein, determining the location of the plurality of infusion pumps in the pump stack includes determining or measuring a head height pressure for each of the infusion pumps, and ordering the infusion pumps from a lowest to highest head height pressure.

In a sixth aspect of the present disclosure, which may be combined with any other aspect, or portion thereof, described herein, a sensor of each infusion pump is configured to measure the respective head height pressure imparted by fluid from the fluid supply container.

In a seventh aspect of the present disclosure, which may be combined with any other aspect, or portion thereof, described herein, the reference infusion pump is determined as having a head height pressure that is within a threshold value of a target fluid pressure.

In an eighth aspect of the present disclosure, which may be combined with any other aspect, or portion thereof, described herein, the target fluid pressure is set to ensure that the reference infusion pump has a flow rate accuracy within a specified range.

In a ninth aspect of the present disclosure, which may be combined with any other aspect, or portion thereof, described herein, the flow rate is adjusted for each infusion pump based on the distance from the reference infusion pump so that the flow rate is within the specified range of the flow rate accuracy.

In a tenth aspect of the present disclosure, which may be combined with any other aspect, or portion thereof, described herein, the distance between each of the infusion pumps and the reference infusion pump is determined based on a known height of each infusion pump and a number of infusion pumps between the reference infusion pump and the respective infusion pump.

In an eleventh aspect of the present disclosure, which may be combined with any other aspect, or portion thereof, described herein, an infusion pump system includes a mounting device, a fluid supply container connected to a top of the mounting device, a first infusion pump connected to the mounting device below the fluid supply container, and a second infusion pump connected to the mounting device below the first infusion pump. The first and second infusion pumps are configured to determine a respective location in a pump stack, determine which of the first and second infusion pumps are a reference infusion pump, and adjust a flow rate of the first or second infusion pump that is not the reference infusion pump based on the distance between the infusion pump and the reference infusion pump.

In a twelfth aspect of the present disclosure, which may be combined with any other aspect, or portion thereof, described herein, determining the location of the first and second infusion pumps in the pump stack includes determining or measuring a head height pressure for each of the first and second infusion pumps, and ordering the first and second infusion pumps from a lowest to greatest head height pressure.

In a thirteenth aspect of the present disclosure, which may be combined with any other aspect, or portion thereof, described herein, a sensor of each of the first and second infusion pumps is configured to measure the respective head height pressure imparted by fluid from the fluid supply container.

In a fourteenth aspect of the present disclosure, which may be combined with any other aspect, or portion thereof, described herein, the reference infusion pump is determined as having a head height pressure that is within a threshold value of a target fluid pressure.

In a fifteenth aspect of the present disclosure, which may be combined with any other aspect, or portion thereof, described herein, the target fluid pressure is set to ensure that the reference infusion pump has a flow rate accuracy within a specified range.

In a sixteenth aspect of the present disclosure, which may be combined with any other aspect, or portion thereof, described herein, the flow rate is adjusted for the first or second infusion pump that is not the reference infusion pump based on the distance from the reference infusion pump so that the flow rate is within the specified range of the flow rate accuracy.

In a seventeenth aspect of the present disclosure, which may be combined with any other aspect, or portion thereof, described herein, the distance between the reference infusion pump and the first or second infusion pump that is not the reference infusion pump is based on a tone generated by the reference infusion pump.

In an eighteenth aspect of the present disclosure, which may be combined with any other aspect, or portion thereof, described herein, the system further includes a third infusion pump connected to the mounting device below the second infusion pump. The first, second, and third infusion pumps are configured to determine a respective location in the pump stack, determine which of the first, second, and third infusion pumps are the reference infusion pump, and adjust a flow rate of the first, second, or third infusion pumps that are not the reference infusion pump based on the distance between the infusion pump and the reference infusion pump.

In a nineteenth aspect of the present disclosure, which may be combined with any other aspect, or portion thereof, described herein, the system further includes a fourth infusion pump connected to the mounting device below the third infusion pump. The first, second, third, and fourth infusion pumps are configured to determine a respective location in the pump stack, determine which of the first, second, third, and fourth infusion pumps are the reference infusion pump, and adjust a flow rate of the first, second, third, and fourth infusion pumps that are not the reference infusion pump based on the distance between the infusion pumps and the reference infusion pump.

In a twentieth aspect of the present disclosure, which may be combined with any other aspect, or portion thereof, described herein, the first and second infusion pumps are communicatively coupled to each other via at least one of a Bluetooth® connection, a Wi-Fi, a near-field communication ("NFC") connection, a serial connection, or a controller area network connection.

In a twenty-first aspect, any of the features, functionality and alternatives described in connection with any one or more of FIGS. 1 to 5 may be combined with any of the features, functionality and alternatives described in connection with any other of FIGS. 1 to 5.

Additional features and advantages of the disclosed method and apparatus are described in, and will be apparent from, the following Detailed Description and the Drawings. The features and advantages described herein are not all-inclusive and, in particular, many additional features and advantages will be apparent to one of ordinary skill in the art in view of the figures and description. Moreover, it should be noted that the language used in the specification has been principally selected for readability and instructional purposes, and not to limit the scope of the inventive subject matter.

BRIEF DESCRIPTION OF THE DRAWINGS

The description will be more fully understood with reference to the following figures, which are presented as exemplary aspects of the disclosure and should not be construed as a complete recitation of the scope of the disclosure, wherein:

FIG. 5 illustrates force differentials based on head height for a device stack, according to example aspects of the present disclosure.

DETAILED DESCRIPTION

Figure 1:
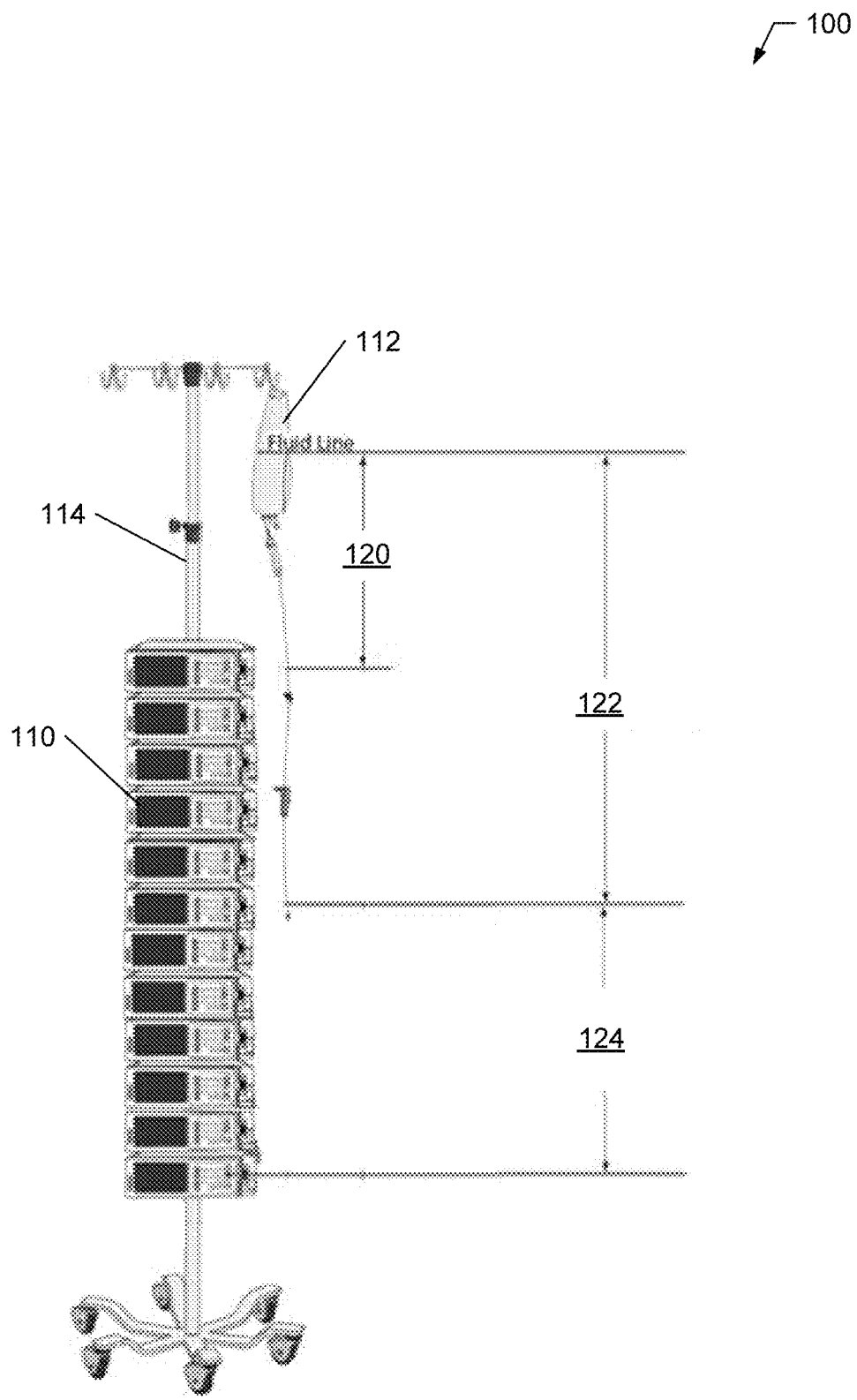
FIG. 1 illustrates a diagram of an infusion pump stack, according to an example aspect of the present disclosure.

Techniques are disclosed for new and innovative systems and methods for flow rate compensation in devices, such as infusion pumps and other electronic devices. Medical devices, such as infusion pumps, can be used to deliver treatments to patients. These treatments typically include delivering medication at a particular flow rate. The infusion pumps are commonly installed on a mobile IV stand, with one or more IV supply containers hung from a top of the mobile IV stand and one or more infusion pumps mounted to a pole in a middle of the mobile IV stand. However, to maintain an accurate flow rate, the infusion pumps typically need to be mounted within a specified distance from the current fluid level in the IV supply container, and this height can change as the location of the infusion pumps and/or fluid level in the IV supply container changes. Flow rate accuracy is necessary to maintain a flow rate of medication within a desirable range. IV bag placement vertically relative to an infusion pump creates a head height pressure for fluid entering the pump. The head height pressure impacts the flow rate accuracy of the infusion pump. Accordingly, IV bag placement relative to an infusion pump is an important parameter for ensuring flow rate accuracy. Typically, the number of infusion pumps in a pump stack can be increased until the accuracy limit of the pumping mechanism is reached. Taller pump stacks beyond this working range are typically not possible or require additional hardware to place the IV supply containers lower, both of which limit environments where maximizing the number of pumps in a vertical direction to maximize floor space efficiency and to minimize the floor cost is desirable. Accordingly, existing techniques are prone to human error resulting in improper set-up of the infusion pumps, resulting in medication delivery outside of a desired flow rate. Additionally, existing techniques add unnecessary cost and complexity to maintain flow rate accuracy for an arbitrarily large stack of infusion pumps.

Systems and methods in accordance with embodiments of the disclosure improve on existing techniques and can automatically maintain a flow rate within a desired flow rate accuracy threshold with little or no user intervention. For example, the techniques disclosed herein enable clinicians to install infusion pumps within a pump stack without manually configuring each of the infusion pumps. Techniques described herein enable the automated identification of a pump's position within a pump stack and/or the relative position of the pump to one or more other pumps in the pump stack. Once the position in stack is known, the flow rate is then adjusted based on a head height range and/or a desired flow rate accuracy. The adjusted flow rate can compensate for the differences in head height pressure between a reference location and an infusion pump, such as a distance from an IV supply container and/or a reference device or pump in the pump stack. These position compensation techniques enable clinicians to place infusion pumps into any position of in a pump stack without any special steps, limitations, or hardware, thereby improving ease of use, increasing the number of infusion pumps that can be incorporated into a pump stack, and improving flow rate accuracy for each infusion pump in the pump stack. This results in a system that is both more economically efficient and improves the ability of the system to deliver treatments to patients.

A variety of systems and processes in accordance with aspects of the disclosure are described in more detail below.

Systems and Devices

FIG. 1 illustrates a diagram of a device stack 100, according to an example aspect of the present disclosure. The device stack 100 includes one or more devices (e.g., infusion pumps) 110 and one or more fluid supply containers (e.g., IV bags) 112 mounted to a mounting device 114. The devices 110 can include a top device, a reference device, a bottom device, and/or a plurality of intermediate devices, as described herein. A distance 120 between the fluid supply containers 112 and a particular device can be used to determine a head height as described herein. For example, the distance 120 can represent the distance between the fluid supply container 112 and a first (top) device in devices 110. Similarly, a distance 122 can represent the distance between the fluid supply containers 112 and a reference device (middle or sixth device from the top) in devices 110. In many embodiments, the reference device is determined as the device in the devices 110 that is a reference distance from the fluid supply container 112. In several embodiments, the reference device is the device that has a fluid pressure within a threshold value of a target fluid pressure, where the target fluid pressure is set to ensure that the device has a flow rate accuracy within a desired range. In many embodiments, at least some of the devices among the devices 110 are located at a distance 124 from the fluid supply container 112. The distance 124 can include distances beyond a specification where the devices 110 can deliver fluid at a flow rate within a desired range using existing techniques. In a variety of embodiments, other devices, such as power supplies providing power to the devices 110, can be incorporated into the device stack 100 as appropriate. In a number of embodiments, the distance 124 is defined as the distance between a reference device and a bottom device in devices 110 or a reference device and devices located below the reference device.

Figure 2:
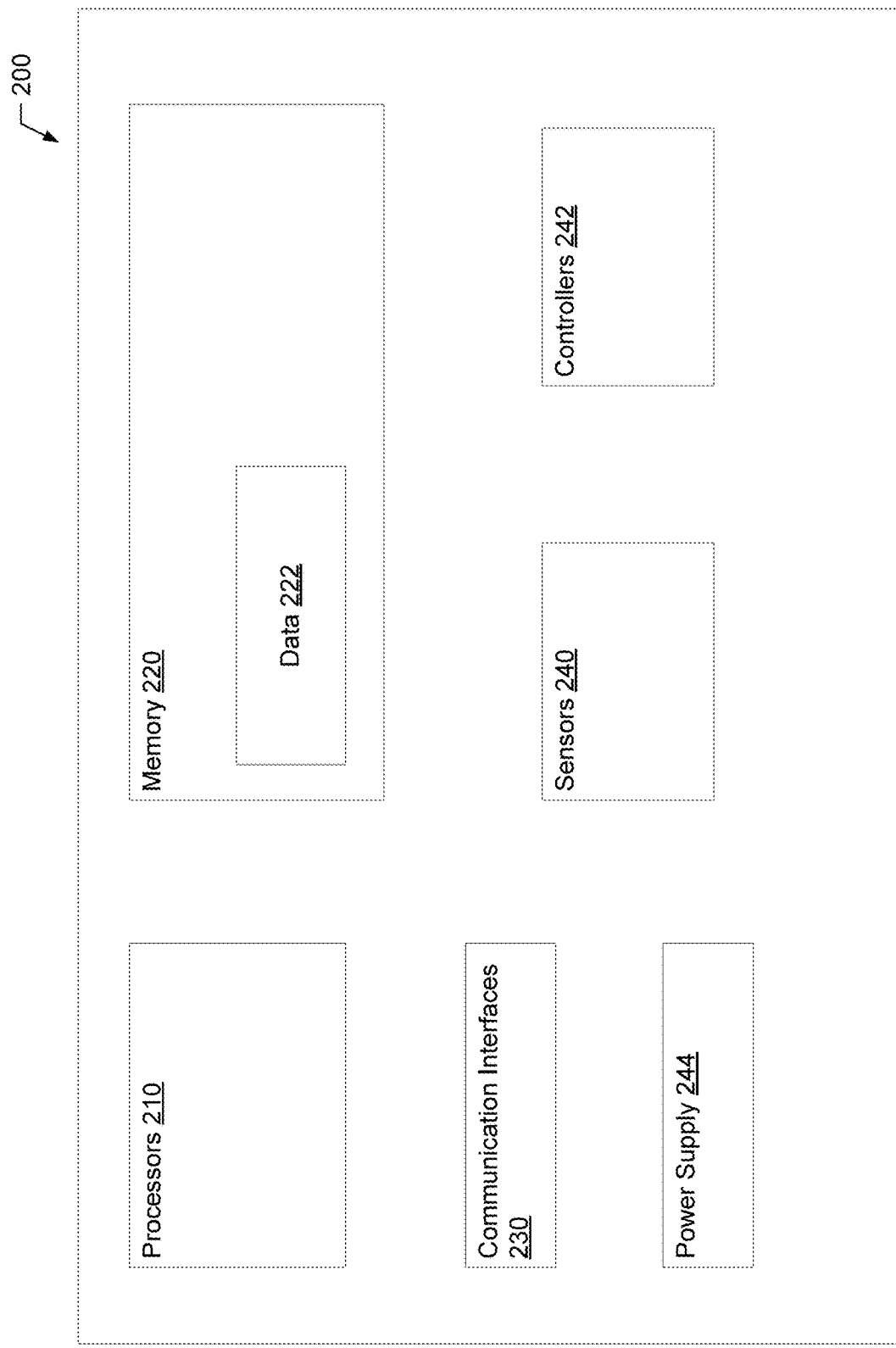
FIG. 2 illustrates a block diagram of an electronic device, such as an infusion pump, according to an example aspect of the present disclosure.

FIG. 2 illustrates a block diagram of an electronic device (e.g., an infusion pump) 200, according to an example aspect of the present disclosure. The device 200 is representative of one or more of the devices 110 of FIG. 1. The device 200 can include processors 210, a memory 220, communication interfaces 230, sensors 240, controllers 242, and/or a power supply 244. The processor 210 may also be referred to as a central processing unit ("CPU"), a logic controller, or a microcontroller. The processor 210 can include one or more devices capable of executing instructions encoding arithmetic, logical, and/or I/O operations. In many aspects, the processor 210 may be a single core processor that is capable of executing one instruction at a time (or process a single pipeline of instructions) and/or a multi-core processor that may simultaneously execute multiple instructions. In a variety of aspects, the processor 210 may be implemented as a single integrated circuit, two or more integrated circuits, and/or may be a component of a multi-chip module in which individual microprocessor dies are included in a single integrated circuit package and hence share a single socket.

The memory 220 can include any combination of volatile and/or non-volatile memory devices, such as RAM, ROM, EEPROM, or any other device capable of storing data. In a number of embodiments, the memory 220 stores a variety of data 222. In a variety of embodiments, the data 222 causes the device 200 to provide one or more application programming interfaces ("APIs") that obtain signals from a variety of devices using the communication interfaces 230. In this way, the device 200 can automatically determine its location within a stack of devices and/or control a flow rate within a desired flow rate accuracy metric. Access to the APIs can be open and/or secured using any of a variety of techniques, such as by using client authorization keys, as appropriate to the requirements of specific applications of the disclosure.

Communication interfaces 230 can include a network device (e.g., a network adapter or any other component that connects a computer to a computer network), a peripheral component interconnect ("PCI") device, storage devices, disk drives, sound or video adaptors, photo/video cameras, printer devices, keyboards, displays, etc. The communications interfaces 230 may communicate via a variety of networks, as appropriate. These networks can include a LAN (local area network), a WAN (wide area network), telephone network (e.g., a Public Switched Telephone Network ("PSTN")), a Session Initiation Protocol ("SIP") network, a wireless network, a point-to-point network, a star network, a token ring network, a hub network, wireless networks (including protocols such as EDGE, 3G, 4G LTE, Wi-Fi, 5G, WiMAX, and the like), the Internet, and the like. A variety of authorization and authentication techniques, such as username/password, Open Authorization ("OAuth"), Kerberos, SecureID, digital certificates, and more, may be used to secure the communications.

The sensor devices 240 may include a variety of sensors configured to sense a variety of environmental and/or physical conditions. In several embodiments, the sensor devices 240 may be used to measure and/or record data regarding a patient being treated for a particular condition. In many embodiments, the sensor devices 240 can detect conditions of a room, such a temperature, humidity, light levels, and the like. In a variety of embodiments, the sensor devices 240 can measure head height pressure, flow rate, flow rate accuracy, and/or signals provided by devices in a device stack, as described herein.

The controllers 242 can include any device used to perform actions, such as electronic components, pumps, actuators, and the like. These actions can include, but are not limited to, adjusting an electrical output of a device, pumping fluid provided by a fluid supply, regulating the delivery of medicine (particularly within a desired flow rate accuracy), altering environmental conditions of a room, and the like. The power supply 244 is configured to provide power to any of the components of the device 200. The power supply 244 can include batteries, capacitors, transformers, charging circuity, and/or any other device capable of providing AC and/or DC power to the components of device 200. In a variety of embodiments, the power supply 244 includes an AC/DC converter that converts AC power into 3.3V, 5V, and/or 12V DC power to the components of device 200. Charging circuity of the power supply 244 can include any suitable charger, such as an AC charger, DC charger, solar panels, and the like.

Although specific architectures for electronic devices in accordance with embodiments of the disclosure are conceptually illustrated in FIG. 2, any of a variety of architectures, including those that store data or applications on a disk or some other form of storage and are loaded into a memory at runtime, can also be utilized. Additionally, any of the data utilized in the system can be cached and transmitted once a network connection (such as a wireless network connection via the communications interface) becomes available. In a variety of embodiments, a memory includes circuitry such as, but not limited to, memory cells constructed using transistors that store instructions. Similarly, a processor can include logic gates formed from transistors (or any other device) that dynamically perform actions based on the instructions stored in the memory. In several embodiments, the instructions are embodied in a configuration of logic gates within the processor to implement and/or perform actions described by the instructions. In this way, the systems and methods described herein can be performed utilizing both general-purpose computing hardware and by single-purpose devices.

Flow Rate Control Processes

Figure 3A:
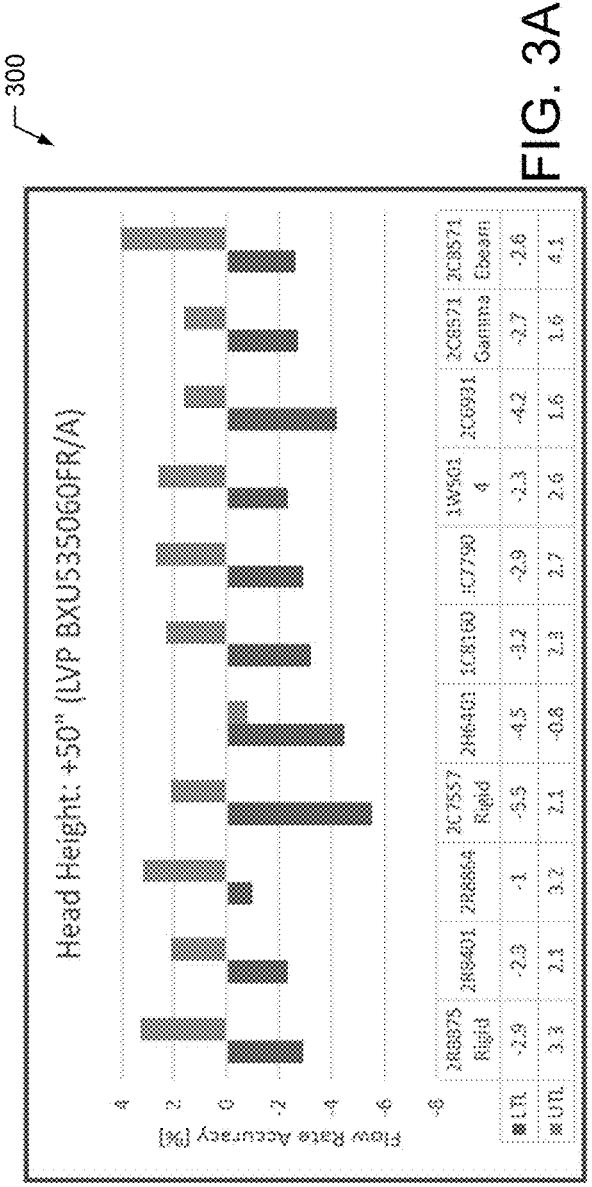
FIGS. 3A-B illustrates examples of flow rate accuracy based on a head height of a fluid supply container, according to example aspects of the present disclosure.
Figure 3B:
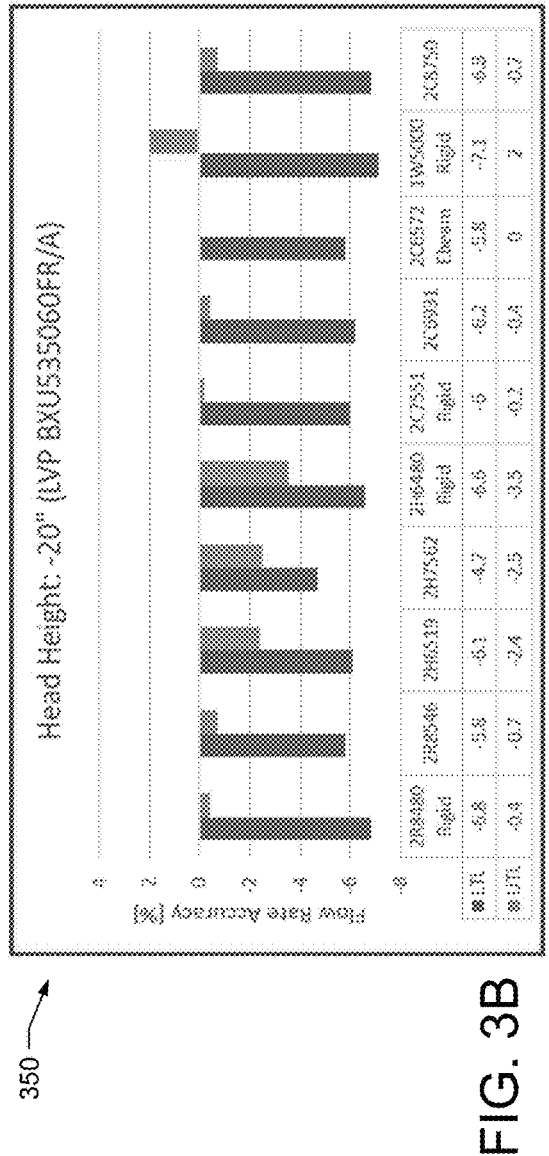

As described herein, it is desirable for infusion pumps (and a variety of electronic devices) to accurately dispense fluid at a flow rate within a specified or programmed flow rate accuracy. Head height pressure (e.g., a distance between the pump and the fluid supply providing the fluid to the pump) can alter the flow volume in a pumping mechanism, which then changes flow rate accuracy. This can be caused, for example, by a higher head height pressure accelerating the recovery of compressed IV tubes and/or a lower head height pressure slowing the recovery of compressed IV tubes. FIGS. 3A-B illustrates examples of flow rate accuracy based on head height, according to example aspects of the present disclosure. FIG. 3A shows a flow rate accuracy table 300 for a head height of +50 inches (e.g., where the pump is 50 inches below the fluid supply) for a variety of different IV tubes. FIG. 3B shows a flow rate accuracy table 350 for a head height of −20 inches (e.g., where the pump is 20 inches above the fluid supply) for a variety of different IV tubes. It should be noted that the flow rate accuracy tables 300 and 350 are provided for explanatory purposes only and that any head heights, IV tubes, and/or flow rate accuracies can be utilized as appropriate.

Infusion pumps (and other electronic devices) can automatically determine their location within a device stack, verify pressure readings using an upstream pressure sensor of each infusion pump, compare the pressure readings of the pumps in the stack, compare an ordering of the pumps in the stack with the position of the infusion pump within the pump stack, identify a pump aligning with a reference head height as a reference pressure and/or a reference infusion pump, and adjust the flow rate of the infusion pump based on its distance from the reference infusion pump so that the flow rate of the infusion pump is within a threshold amount of a desired flow rate accuracy. In a variety of embodiments, the reference infusion pump is programmed to deliver a fluid flow at a particular rate based on the fluid supply, while the remaining pumps in the device stack are configured to automatically adjust their operation to match the flow rate and flow rate accuracy of the reference infusion pump.

Figure 4:
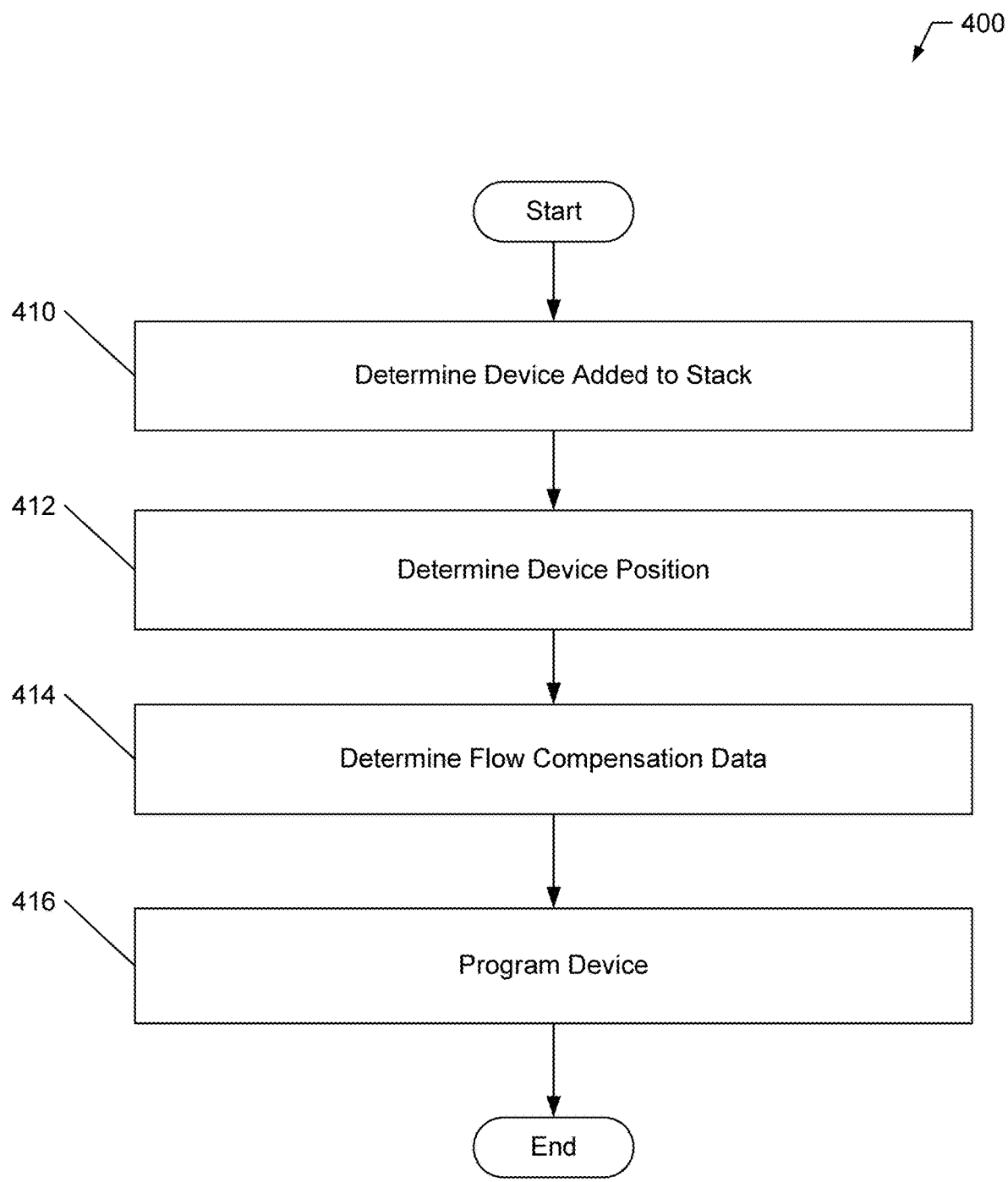
FIG. 4 illustrates a flowchart of a flow rate control process, according to an example aspect of the present disclosure.

FIG. 4 illustrates a flowchart of a flow rate control process, according to an example aspect of the present disclosure. Although the process 400 is described with reference to the flowchart illustrated in FIG. 4, it should be appreciated that many other methods of performing the acts associated with the process 400 may be used. For example, the order of some of the blocks may be changed, certain blocks may be combined with other blocks, one or more blocks may be repeated, and some of the blocks described are optional. The process 400 may be performed by processing logic (e.g., the processor 210 of FIG. 2) that may include hardware (circuitry, dedicated logic, etc.), software, or a combination of both.

The process 400 includes determining (410) that a device has been added to a device stack. The device can be an infusion pump and the device stack can be a stack of infusion pumps, as described herein. Determining (410) that a device has been added to a device stack can include, but is not limited to, using one or more sensors located in the device to determine that it has been mounted to a mounting device, that there is another device/infusion pump located above and/or below the device, and/or that a fluid supply container has been connected to the device. In many embodiments, determining (410) that a device has been added to a device stack includes receiving signals that can be used to determine (412) a position of the device within the device stack. It should be noted that, in a variety of embodiments, the device can already be present in the device stack when the signals are received.

A device position can be determined (412). The device position can be determined (412) within the device stack. In a variety of embodiments, head height pressure can be measured for each device and used to establish the position of each device in the stack, such as illustrated in FIG. 5. FIG. 5 illustrates force differentials based on head height for a device stack, according to example aspects of the present disclosure. It should be noted that the force differential table 500 is provided for explanatory purposes only and that any number of pumps, reference heights and/or pressures, and/or forces can be utilized as appropriate. Each device can determine its head height pressure and transmit its pressure and/or a device identifier to the other devices within the device stack using any communication channels as described herein. In many embodiments, these communication channels can include, but are not limited to, Bluetooth®, Wi-Fi, near-field communication ("NFC"), a serial connection, a controller area network connection, direct electrical contacts, optical communication channels including LED and photodiode communication channels, and contactless radio frequency ("RF") connections. The head height pressure can be determined based on the distance from a fluid supply container to the device, the type of IV tube used to connect the fluid supply to the device, the diameter of the of the IV tube, and/or any of a variety of criteria as appropriate. Each device can order the devices by their head height pressure (e.g., high to low, low to high, and the like).

In several embodiments, an ambient light sensor can be used to detect device location within the device stack. The ambient light sensor can determine, based on a reference light level, how much light is reaching the sensors, which can be used to calculate a number of devices located above the device.

In a number of embodiments, each device can include a speaker and a microphone used to detect pump position. The speaker can be used to generate a reference tone on a first device, which can be measured using the microphone on a second device. For example, each device can play the reference tone in a serial order such that each device can identify one device located above (or below) the device. By identifying the adjacency of devices, a top device (e.g. a device with no other devices above it) and a bottom device (e.g. a device with no other devices below it) can be determined. The pairwise adjacency of devices can then be used to iteratively (and/or recursively) determine the ordering of the devices within the device stack. For example, each device can generate a unique tone at a specified volume and/or frequency and produce the tone via its speaker. Each device in the device stack can receive each of the unique tones using its microphone and, based on the difference in volume and/or frequency between the received tone and the specified volume and/or frequency for a particular device, a distance between the microphone and the speaker generating the tone can be determined. These distances can be used to determine the relative ordering of the devices within the device stack.

In another embodiment, the devices may be connected to communication bus via respective ports on a rack. Each port may be assigned an identifier. Since a location of each port relative to the rack is known, the identifiers of the ports may be used by the devices to determine a location on the rack. The devices may transmit or broadcast messages indicative of their port identifier. Each device may use the received identifiers to determine its position. Further, when a distance from a fluid supply container is known, the devices may automatically determine their respective distances from the fluid supply container for estimating head height pressure.

Returning to FIG. 4, flow compensation data can be determined (414). The flow compensation data can be determined based on the head height pressure for a particular device, the head height pressure for a reference device, a distance between the device and a reference device, and/or a variety of other criteria as described herein. In many embodiments, a reference device can be determined based on the device within the device stack having a head height pressure equal or within a threshold amount from a reference pressure. In a number of embodiments, the reference pressure is 6.81 grams. In a variety of embodiments, each device has a known height and the distance between a target device and the reference device can be calculated based on the number of devices between the reference device and the target device. The flow compensation data can be determined (414) such that the flow rate for the device remains within a flow rate accuracy threshold of a target flow rate. The target flow rate and/or flow compensation data can be determined (414) based on the head height pressure of the device, the distance of the device from the reference device, the head height pressure and/or flow rate of the reference device, a desired flow rate for a particular fluid supply, and/or any other data as appropriate.

The device can be programmed (416). The device can be programmed (416) based on the flow compensation data. The flow compensation data can cause a pump in the device to adjust its operation to maintain the desired flow rate and/or desired flow rate accuracy, as described herein. In several embodiments, the flow compensation data includes instructions that, when read by a controller and/or a processor, modify the operation of the pump. In many embodiments, the device automatically programs (416) to match the operation of a reference device in the device stack.

It should be appreciated that all of the disclosed methods and procedures described herein can be implemented using one or more computer programs, components, and/or program modules. These components may be provided as a series of computer instructions on any conventional computer readable medium or machine-readable medium, including volatile or non-volatile memory, such as RAM, ROM, flash memory, magnetic or optical disks, optical memory, or other storage media. The instructions may be provided as software or firmware and/or may be implemented in whole or in part in hardware components such as ASICs, FPGAs, DSPs or any other similar devices. The instructions may be configured to be executed by one or more processors, which when executing the series of computer instructions, performs or facilitates the performance of all or part of the disclosed methods and procedures. As will be appreciated by one of skill in the art, the functionality of the program modules may be combined or distributed as desired in various aspects of the disclosure.

Although the present disclosure has been described in certain specific aspects, many additional modifications and variations would be apparent to those skilled in the art. In particular, any of the various processes described above can be performed in alternative sequences and/or in parallel (on the same or on different computing devices) in order to achieve similar results in a manner that is more appropriate to the requirements of a specific application. It is therefore to be understood that the present disclosure can be practiced otherwise than specifically described without departing from the scope and spirit of the present disclosure. Thus, embodiments of the present disclosure should be considered in all respects as illustrative and not restrictive. It will be evident to the annotator skilled in the art to freely combine several or all of the embodiments discussed here as deemed suitable for a specific application of the disclosure. Throughout this disclosure, terms like "advantageous", "exemplary" or "preferred" indicate elements or dimensions which are particularly suitable (but not essential) to the disclosure or an embodiment thereof, and may be modified wherever deemed suitable by the skilled annotator, except where expressly required. Accordingly, the scope of the disclosure should be determined not by the embodiments illustrated, but by the appended claims and their equivalents.

What is claimed is:

1. An infusion pump system comprising:
a mounting device;
a fluid supply container connected to a top of the mounting device;
a first infusion pump connected to the mounting device below the fluid supply container; and
a second infusion pump connected to the mounting device below the first infusion pump,
wherein the first and second infusion pumps are configured to:
determine a respective location in a pump stack;
determine which of the first and second infusion pumps are a reference infusion pump by determining which of the first and second infusion pumps is a reference distance from the fluid supply container; and
adjust a flow rate of the other of the first or second infusion pump, that is not the reference infusion pump, based on a distance between the other infusion pump and the reference infusion pump.

2. The system of claim 1, wherein determining the location of the first and second infusion pumps in the pump stack includes:
determining or measuring a head height pressure for each of the first and second infusion pumps; and
ordering the first and second infusion pumps from a lowest to highest head height pressure.

3. The system of claim 2, wherein a sensor of each of the first and second infusion pumps is configured to measure the respective head height pressure imparted by fluid from the fluid supply container.

4. The system of claim 2, wherein the reference distance for the reference infusion pump is determined as having a head height pressure that is within a threshold value of a target fluid pressure.

5. The system of claim 4, wherein the target fluid pressure is set to ensure that the reference infusion pump has a flow rate accuracy within a specified range.

6. The system of claim 5, wherein the flow rate is adjusted for the first or second infusion pump that is not the reference infusion pump based on the distance from the reference infusion pump so that the flow rate is within the specified range of the flow rate accuracy.

7. The system of claim 1, wherein the distance between the reference infusion pump and the first or second infusion pump that is not the reference infusion pump is based on a tone generated by the reference infusion pump.

8. The system of claim 1, further comprising a third infusion pump connected to the mounting device below the second infusion pump,
wherein the first, second, and third infusion pumps are configured to:
determine a respective location in the pump stack;
determine which of the first, second, and third infusion pumps are the reference infusion pump; and
adjust a flow rate of each of the other two of the first, second, or third infusion pumps, that are not the reference infusion pump, based on respective distances between respective ones of the other two infusion pumps and the reference infusion pump.

9. The system of claim 8, further comprising a fourth infusion pump connected to the mounting device below the third infusion pump,
wherein the first, second, third, and fourth infusion pumps are configured to:
determine a respective location in the pump stack;
determine which of the first, second, third, and fourth infusion pumps are the reference infusion pump; and
adjust a flow rate of each of the other three of the first, second, third, and fourth infusion pumps, that are not the reference infusion pump based on respective distances between respective one of the other three infusion pumps and the reference infusion pump.

10. The system of claim 1, wherein the first and second infusion pumps are communicatively coupled to each other via at least one of a Bluetooth® connection, a Wi-Fi, a near-field communication ("NFC") connection, a serial connection, or a controller area network connection.

* * * * *